ized Patent [19]

United States Patent [19]
Lee

[11] 3,959,495
[45] May 25, 1976

[54] RECONSTITUTION OF DRY YEAST IN DOUGH PREPARATION

[75] Inventor: John L. Lee, Menstrie, Scotland

[73] Assignee: The Distillers Company (Yeast) Limited, Morden, England

[22] Filed: July 22, 1974

[21] Appl. No.: 490,444

[30] Foreign Application Priority Data
July 23, 1973 United Kingdom............... 34947/73

[52] U.S. Cl.................................... 426/24; 426/62
[51] Int. Cl.².............................................. A21D 2/16
[58] Field of Search...................... 426/24, 62, 152; 195/74

[56] References Cited
UNITED STATES PATENTS
3,407,072   10/1968   Aizawa et al. .................. 426/62
3,448,010   6/1969   Pomper et al. .................. 426/62 X FOREIGN PATENTS OR APPLICATIONS
45-16770   1970   Japan.................................. 426/62

OTHER PUBLICATIONS

"Dry Yeast Additive", Food Engineering, Vol. 38, No. 3, p. 28, Mar. 1966.

Primary Examiner—James R. Hoffman
Attorney, Agent, or Firm—Lawrence Rosen; E. Janet Berry

[57] ABSTRACT

When making dough using active dried yeast the yeast is reconstituted in an emulsion of an ester of a polyglycerol with saturated fatty acid or of an ester of sorbitan or hexitan with a saturated $C_{16}$ to $C_{18}$ fatty acid.

5 Claims, No Drawings

RECONSTITUTION OF DRY YEAST IN DOUGH PREPARATION

It is well-known to produce bakers's yeast in dry particulate form, the resultant baker's yeast being known as "active dried yeast". Such yeast has a dry matter content greater than 90% by weight, often 93–96% by weight. Active dried yeast is made by various methods, for example extrusion into pellet form followed by drum drying or by methods which produce powdered materials, that is to say materials having a much lighter and more powdery texture than conventional pellets.

In the production of a dough from flour, water and active dried yeast it is necessary that the yeast should be reconstituted. Normally reconstitution is brought about by initially soaking the yeast in water prior to adding flour. Some of the powdered forms of active dried yeast can be reconstituted merely by contact with the flour, optionally in the presence of water. Although this property is often advantageous it is sometimes in practice undesirable to have to modify certain modern industrial baking processes, such as the Chorleywood process, to permit this reconstitution to occur in the presence of flour.

In the invention the active dried yeast is, before being mixed with the bulk of the flour to form the dough, added to and reconstituted in an emulsion in water of an ester of (1) polyglycerol with saturated fatty acid, or (2) a sorbitan or hexitan with saturated $C_{16}$ to $C_{18}$ fatty acid. We find the invention results in improved activity.

(1) may be formed by esterifying a mixture of polyglycerols with a $C_{16}$ to $C_{18}$ fatty acid, for example with palmitic acid or stearic acid or with mixtures consisting predominantly of either or both of these. The resultant product is mainly a monoester although it does contain some di or higher esters and it also contains some, e.g. up to 10%, unesterified fatty acid. A suitable material is sold under the trade name "ADMUL Polyester 57" made by Food Industries Limited and the preparation of this is described in Pages 27 and 28 of Process Biochemistry, December 1972. This is a mixture of esters of mixed polymers of glycerol with a mixture of fatty acids, mainly stearic, having a slip point of 54°–58°C.

(2) is generally a mixed ester both of sorbitans (these being 1,4-anhydroglucitol and 3,6-anhydroglucitol) and isosorbide (this being 1,4-; 3,6-dianhydroglucitol). The fatty acid used for forming the ester is generally palmitic or stearic acid or mixtures consisting predominantly of either or both of these. The product is mainly a mixed monoester and diester and generally also contains some, e.g. up to 2%, free fatty acid. The production of suitable esters is described in U.S. patent specification No. 2,322,821. Suitable materials are available under the trade names "SPAN 40" and "SPAN 60". "Span" 40 contains about 35% or less of each of the mono- and dipalmitate and up to 2% of the free acid, with the balance unreacted sugar alcohol and anhydride. "Span" 60 contains about 45% or less each of the mono- and distearate and up to 2% of the free acid, with the balance unreacted sugar alcohol and anhydride. Other products that may be used are the corresponding esters of hexitans and hexides, for example obtained by esterification of mannitol or other hexitol.

The ester is present in the water used for reconstitution as a dilute aqueous emulsion before addition of the yeast. This dilute emulsion is usually formed by combining the ester in the form of a more concentrated emulsion with the water.

The reconstitution is preferably initiated by adding the active dried yeast to the dilute aqueous emulsion which preferably has a temperature of from 30°–45°C, most preferably about 38°C. The dilute aqueous emulsion may contain from 0.1 to 10% by weight of the ester (i.e. the mixture containing the esters) most preferably from 0.3 to 1%. The amount of active dried yeast added to the dilute aqueous emulsion is normally, per 100 parts by weight of the emulsion, from 0.5 to 30 parts, preferably 1–10 parts and most preferably 2 to 5 parts by weight on a dry weight basis.

During reconstitution the dilute aqueous emulsion often contains only the esters and the yeast, at least at the start. Even if it does contain any flour, the amount compared to the total amount required for the final dough will be small, e.g. less than 20% and preferably less than 10% by weight based on the weight of water.

The duration of the reconstitution, i.e. the interval between contacting the yeast with water and additive and adding the flour needed for forming the dough is generally up to 30 minutes. Preferably reconstitution is conducted for from 10 to 20 minutes, e.g. 15 minutes, in the water and additive alone and then other materials may be added. For example salt and further water may be added. Flour to form the dough is usually added subsequently.

The invention is of value in any bakery process using active dried yeast, including activated dough development processes using 1-cysteine. It is of particular value in the Chorleywood Break-making process and in similar commercial fast processes. In this and similar processes the normal method, using moist compressed yeast, comprises adding the yeast and other components, such as salt, to the mixer. Water and flour are then added in that order or simultaneously and the whole is mixed to form the dough which is subsequently baked to form a baked product. In order to adapt this process to operate in accordance with the invention it is desirable to provide a second vessel in which the reconstitution can be effected. This vessel may serve solely as a reconstitution vessel, its contents being metered into the dough mixer together with additional water prior to adding the flour in the normal way.

The yeast can be a pellet yeast, for example a drum dried pellet yeast, but preferably is a powdered yeast, for example having a particle size of 1.7 mm or less. One preferred way of making powdered yeast comprises spray drying a liquid yeast composition in air, optionally followed by further drying. For example a liquid yeast may be spray dried, for example to a dry matter content of 40 – 50% dry matter, and may then be further dried, for example in a fluidised bed. Such a process is described in British patent specification No. 1,196,786. Another preferred method comprises comminuting moist yeast, for example having a dry matter content of 27 – 40% by weight, under conditions of high shear followed by drying, for example in a fluidised bed or in trays. Comminution can for example be in a mill, for example containing blades that rotate at a speed greater than 2,000 r.p.m. Suitable processes are described in British patent specification No. 1,140,016 and Belgian patent specification No. 797,062 (equivalent to British patent application No. 41144/72).

The following are some examples of the invention.

EXAMPLE 1

1.8 grams of active dried yeast made by the process described in Belgian patent specification No. 797,062 were added to 50 ml of a 0.5% weight/volume aqueous emulsion of Span 40 warmed to 38°C. After 15 minutes, water and salt solutions were added to yield a total valuem of 100 ml and flour was then added to 15 ml of this suspension to form a dough, all as in the fermentometer test as described in J. Inst. Brew 65,39–45(1959). The activity obtained in the 90 minute test was 111 ml.

When Span 40 was replaced with Span 20 and Span 80 respectively the 90 minute activities measured were 85 and 97 ml. When reconstitution was in water alone, without Span 40 being present, the 90 minute activity was 107 ml.

EXAMPLE 2

1.8 grams of active dried yeast of a different strain but made by the same general method as in Example 1 was added to 87 ml of a 0.5% weight/volume aqueous emulsion of Admul 57 warmed to 38°C. Further processing was as in Example 1. The 90 minute activity was 87 ml.

When this process was repeated reconstituting the yeast in water alone, without Admul 57, the 90 minute activity was 80 ml.

I claim:

1. A process for making a dough comprising mixing active dried yeast, flour and water in which the yeast is, before being mixed with the bulk of the flour to form dough, added to and reconstituted in an emulsion in water of an ester of polyglycerol with a saturated fatty acid.

2. A process according to claim 1 in which the ester is the ester of a mixture of polyglycerols with a $C_{16}$ to $C_{18}$ fatty acid or with a mixture of such acids and contains monoester, unesterified fatty acid and higher esters.

3. A process according to claim 1 in which the reconstitution is conducted at a temperature of 30° to 45°C. in an aqueous emulsion containing from 0.3 to 1% by weight of the ester using 1–10 parts by weight, on a dry weight basis, of the yeast per 100 parts by weight of the emulsion for up to 30 minutes.

4. A process according to claim 3 in which the reconstitution is conducted for 10 to 20 minutes at a temperature of about 38°C.

5. A process according to claim 1 in which the active dried yeast is a powdered yeast.

* * * * *